United States Patent
Lu

(10) Patent No.: US 8,360,241 B2
(45) Date of Patent: Jan. 29, 2013

(54) METHOD FOR MANAGING DRIP INFUSION STANDS

(76) Inventor: Kun-Chung Lu, Kaohsiung Hsien (TW)

( * ) Notice: Subject to any disclaimer, the term of this patent is extended or adjusted under 35 U.S.C. 154(b) by 169 days.

(21) Appl. No.: 12/947,208

(22) Filed: Nov. 16, 2010

(65) Prior Publication Data

US 2011/0127199 A1   Jun. 2, 2011

(30) Foreign Application Priority Data

Nov. 27, 2009   (TW) ............................... 98140498 A

(51) Int. Cl.
*B07C 5/02* (2006.01)
(52) U.S. Cl. ............................... 209/3.3; 209/9; 209/702
(58) Field of Classification Search .................... 209/3.3, 209/702; 211/22, 85.13; 248/688
See application file for complete search history.

(56) References Cited

U.S. PATENT DOCUMENTS

| | | | | |
|---|---|---|---|---|
| 5,048,585 A | * | 9/1991 | Miller | 160/135 |
| 7,166,205 B2 | * | 1/2007 | Kuo et al. | 205/174 |
| 2001/0045378 A1 | * | 11/2001 | Charles et al. | 209/3.3 |
| 2006/0101856 A1 | * | 5/2006 | Lehman et al. | 65/29.11 |

FOREIGN PATENT DOCUMENTS

DE   202009009798   * 7/2009

* cited by examiner

*Primary Examiner* — Terrell Matthews
(74) *Attorney, Agent, or Firm* — Muncy, Geissler, Olds & Lowe, PLLC

(57) ABSTRACT

A method for managing drip infusion stands aims to set different colors for drip infusion stands according to requirements of varying departments in a hospital. The drip infusion stand is made of aluminum alloy and includes a telescopic upright post with the surface treated by an anodizing process to form a selected color to match the department. Thus the mixed drip infusion stands can be easily distinguished and sorted out by management staffs according to the colors to return to the departments they belong. Time for returning the drip infusion stands to the varying departments is shortened and management of the drip infusion stands is more efficient. The problem of shortage of drip infusion stands in certain departments or floors in the hospital also can be averted.

2 Claims, 3 Drawing Sheets

METHOD FOR MANAGING DRIP INFUSION STANDS

FIELD OF THE INVENTION

The present invention relates to a method for managing drip infusion stands and particularly to a method that forms different colors on the surface of telescopic upright posts of the drip infusion stands made of aluminum alloy through an anodizing process according to preset colors of varying departments in a hospital to improve drip infusion stand management efficiency.

BACKGROUND OF THE INVENTION

Many inpatients hospitalized in various departments or floors often get an intravenous infusion. The intravenous infusion often consumes a long duration. When the inpatient getting the intravenous infusion wants to leave the sickbed and go around, a drip infusion stand is needed to hang the drip bottle during moving of the inpatient. As a result, the drip infusion stands could be moved and placed in different departments or floors. The conventional drip infusion stands usually are formed in single color and style, and difficult to distinguish the departments or floors they belong. Hence some departments or floors could have shortage of drip infusion stands, and managing the drip infusion stands becomes difficult.

A conventional drip infusion stand 10 commonly used in hospitals, referring to FIG. 1, includes a foot stand 11 and an upright post 12 mounted thereon. The upright post 12 is extended upwards to a selected height and coated with baking lacquers on the outer surface. The baking lacquers tend to be peeled off upon impact. The upright post 12 has the top end fastened a drip suspension rod 13 by soldering. The conventional drip infusion stand 10 usually is monochromatic and difficult to distinguish which department or floor it belongs. Hence it is difficult to instantly return the drip infusion stand 10 to its original department. It often happens that some departments or floors have shortage of the drip infusion stand 10.

SUMMARY OF THE INVENTION

The present invention aims to solve the problems occurred to the conventional hospitals that have drip infusion stands mixed up and result in shortage in some departments or floors, cause management difficult, and peeling off of the baking lacquers on the surface of the drip infusion stands upon impact by providing a method for managing drip infusion stands that forms different colors on the surface of telescopic upright posts of the drip infusion stands made of aluminum alloy through an anodizing process according to preset colors of varying departments in a hospital to improve drip infusion stand management efficiency and also provide greater abrasion resistance to prevent the surface of the telescopic upright posts from wearing or peeling off during telescopic movements.

The method according to the invention includes forming different colors on the surface of telescopic upright posts of drip infusion stands made of aluminum alloy through an anodizing process according to required preset colors of varying departments in a hospital, so that in the event that the drip infusion stands of varying departments are mixed up, they can be easily sorted out and returned to the departments they belong.

The dyeing layer on the surface of the telescopic upright posts formed by the anodizing process can be instantly sorted out by management staffs according to color classification of varying departments so that they can be returned to their respective department. By forming the dyeing layer on the surface of the telescopic upright posts through the anodizing process, greater abrasion resistance can be achieved to prevent the dyeing layer from wearing or peeling off during the telescopic movements of the upright posts, and durability also improves.

The method for managing drip infusion stands provided by the invention can achieve many benefits, notably:

1. The drip infusion stands are preset to different colors according to requirements of varying departments in the hospital, and the surface of the telescopic upright posts of the drip infusion stands made of aluminum alloy is formed in different colors by the anodizing process according to the preset colors of varying departments, thus mixed drip infusion stands can be easily sorted out by management staffs and returned to where they belong in a shorter time, and also prevent the problem of shortage of the drip infusion stands in some departments or floors, and management efficiency of the drip infusion stands greatly improves.

2. The telescopic upright post has the surface treated by the anodizing process to form the dyeing layer which has greater abrasion resistance, thus can withstand wearing during telescopic movements or impact without peeling off, and also improve durability of the drip infusion stand.

3. The colored telescopic upright posts can be distinguished easily according to preset colors of varying departments in the hospital, so that the drip infusion stands can be instantly sorted out from a mixed condition to return the drip infusion stands to their respective department to facilitate management.

The foregoing, as well as additional objects, features and advantages of the invention will be more readily apparent from the following embodiment and detailed description, which proceeds with reference to the accompanying drawings.

DETAILED DESCRIPTION OF THE PREFERRED EMBODIMENT

Figure 1:
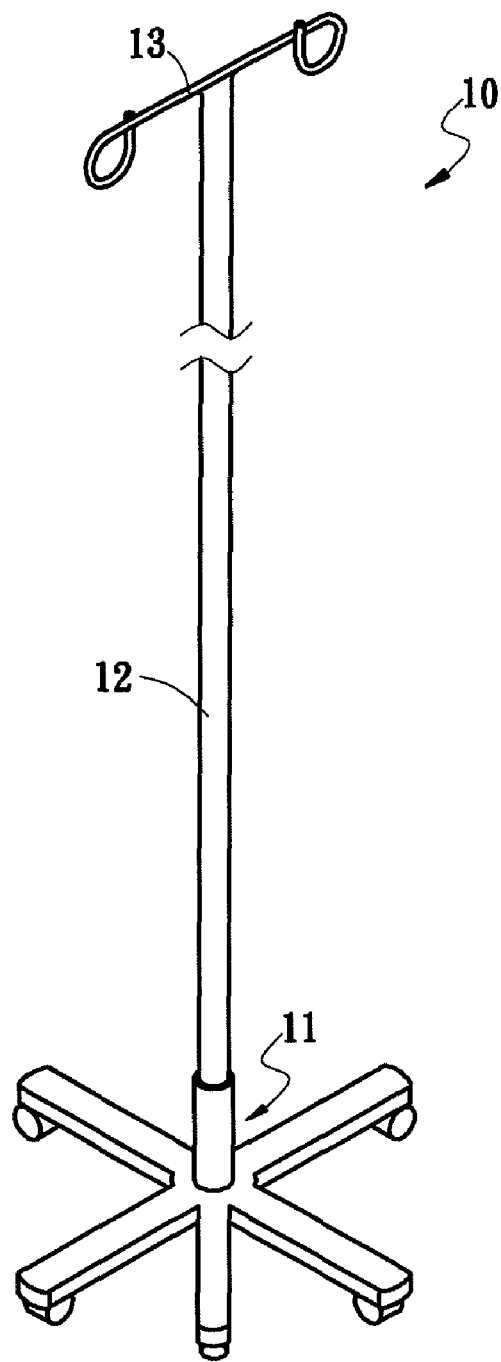
FIG. 1 is a perspective view of a conventional drip infusion stand.
Figure 2:
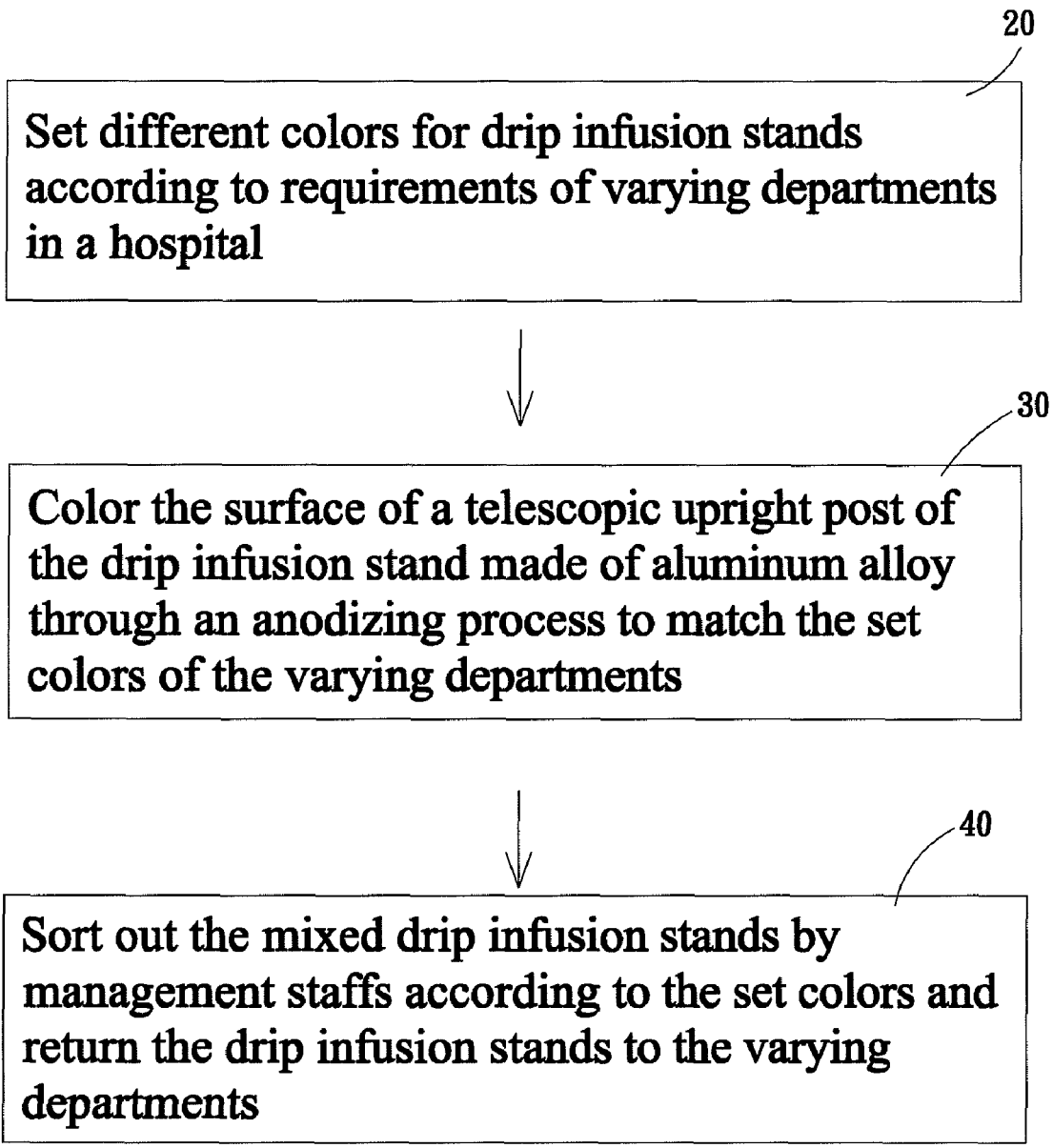
FIG. 2 is a flowchart of the method for managing drip infusion stands according to the invention.

Please refer to FIG. 2 for the flowchart of the method for managing drip infusion stands of invention. It includes step 20 for setting different colors for drip infusion stands according to requirements of varying departments in a hospital; step 30 for coloring the surface of telescopic upright posts of the drip infusion stands made of aluminum alloy through an anodizing process to match the set colors of the varying departments; and step 40 for sorting out the mixed drip infusion stands according to different colors by management staffs and returning the drip infusion stands 50 to the respective departments. Thus the drip infusion stands 50 belonged to varying departments can be easily distinguished and returned to facilitate management.

Figure 3:
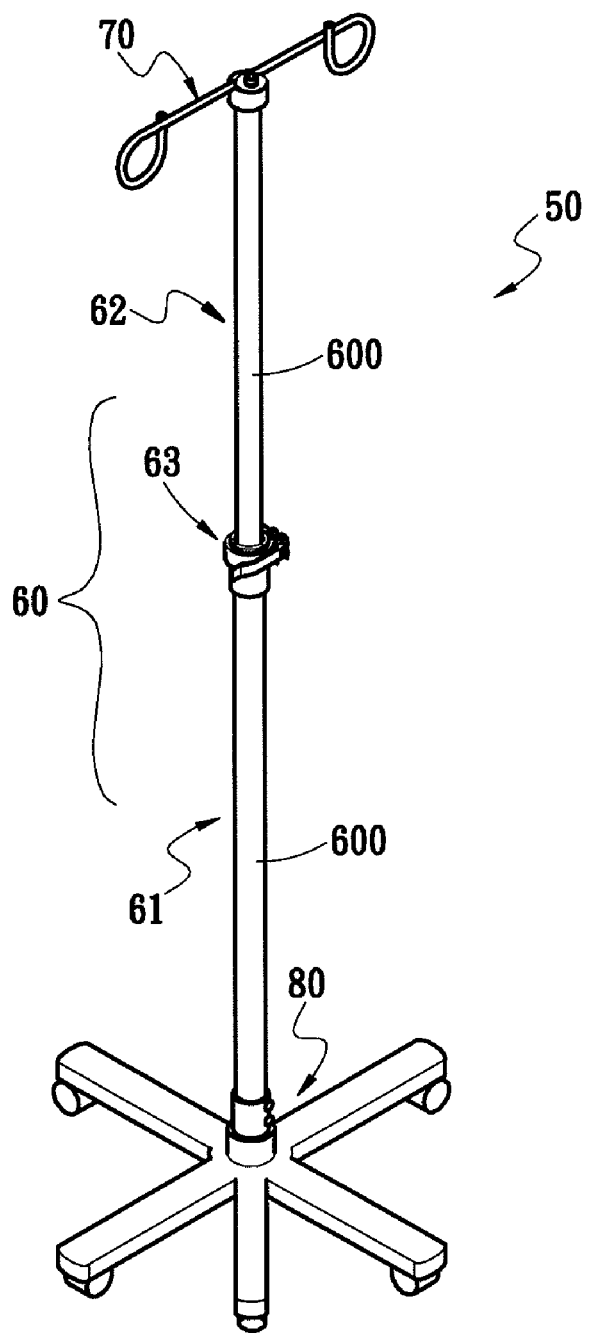
FIG. 3 is a perspective view of the drip infusion stand of the invention.

Referring to FIG. 3, according the method of the invention, the drip infusion stand 50 made of aluminum alloy includes a telescopic upright stand 60 with the surface treated by an anodizing process to form a desired color mating varying departments in the hospital. Hence the colored drip infusion stands 50 can be easily distinguished and sorted out to be returned to the departments they belong. Time for returning can be reduced, and the problem of shortage of the drip infusion stands 50 in certain departments or floors can be averted.

The drip infusion stand 50 of the invention further includes a latch member 63 on the telescopic upright post 60 and a drip suspension portion 70 at the top end of the upright post 60. The latch member 63 and drip suspension portion 70 may also be colored by anodizing to form a color the same as that of the telescopic upright post 60 to make management of the drip infusion stands 50 more efficient.

Refer to FIG. 3 for an embodiment of the drip infusion stand 50 of the invention. The drip infusion stand 50 is made of aluminum alloy with a dyeing layer 600 on the surface formed through an anodizing process in a selected color according to requirements of varying departments in the hospital.

Referring to FIG. 3, the telescopic upright post 60 further includes a first upright post 61 and a second upright post 62 which is telescopic in the first upright post 61 to a desired height or according to inpatient's moving requirements, and then can be fastened and anchored through the latch member 63. The surfaces of the first upright post 61 and second upright post 62 also have the dyeing layers 600 formed thereon by anodizing. Thus the drip infusion stands 50 can be quickly distinguished and sorted out to return to the departments or floors they belong to facilitate management. As the dyeing layer 600 on the surface of the telescopic upright post 60 is formed by anodizing, it has greater abrasion resistance and can withstand wearing during repetitive telescopic movements and impact without peeling off, thus durability of the drip infusion stand 50 also improves.

The drip infusion stand 50 of the invention, in addition to the telescopic upright post 60 with the surface formed by the anodized dyeing layer 600, may also have the anodized dyeing layer 600 formed on the latch member 63 and drip suspension portion 70 at the top end of the telescopic upright post 60 to further improve the classification of the mixed drip infusion stands 50 to return to the varying departments, thus management of the drip infusion stands 50 is more efficient.

What is claimed is:

1. A method for managing drip infusion stands, comprising steps of:
    setting different colors for drip infusion stands according to requirements of varying departments in a hospital;
    coloring the surface of a telescopic upright post of the drip infusion stand made of aluminum alloy to form a selected color mating each department through an anodizing process; and
    sorting out the mixed drip infusion stands by management staffs according to the set colors and returning the sorted drip infusion stands to the belonged departments.

2. The method for managing drip infusion stands of claim 1, wherein the drip infusion stand further includes a latch member on the telescopic upright post and a drip suspension portion at the top end of the telescopic upright post that are selectively colored by the anodizing process to match the color of the telescopic upright post.

\* \* \* \* \*